(12) United States Patent
Yasunaga

(10) Patent No.: US 6,505,461 B1
(45) Date of Patent: Jan. 14, 2003

(54) DRUG INSPECTION DEVICE AND DRUG PACKAGING DEVICE

(75) Inventor: Itsuo Yasunaga, Toyonaka (JP)

(73) Assignee: Kabushiki Kaisha Yuyama Seisakusho, Osaka (JP)

( * ) Notice: Subject to any disclaimer, the term of this patent is extended or adjusted under 35 U.S.C. 154(b) by 0 days.

(21) Appl. No.: 09/504,870

(22) Filed: Feb. 16, 2000

Related U.S. Application Data

(60) Division of application No. 09/301,335, filed on Apr. 29, 1999, which is a continuation-in-part of application No. 08/978,605, filed on Nov. 26, 1997, now abandoned.

(30) Foreign Application Priority Data

Nov. 29, 1996 (JP) .............................................. 8-319226

(51) Int. Cl.⁷ ................................................ B65B 43/02
(52) U.S. Cl. .............................. 53/562; 53/55; 382/141
(58) Field of Search ................................ 382/118, 141, 382/143; 348/129; 700/216, 220; 53/562, 52, 55, 459

(56) References Cited

U.S. PATENT DOCUMENTS

| | | | | |
|---|---|---|---|---|
| 5,274,984 A | * | 1/1994 | Fukuda | |
| 5,626,001 A | * | 5/1997 | Belec | |
| 5,671,592 A | * | 9/1997 | Yuyama et al. | |
| 5,832,693 A | * | 11/1998 | Yuyama et al. | |
| 5,946,883 A | * | 9/1999 | Yuyama et al. | |
| 6,115,996 A | * | 9/2000 | Yuyama et al. | |
| 6,272,816 B1 | * | 8/2001 | Viaud et al. | |

FOREIGN PATENT DOCUMENTS

JP          7282219          * 10/1995

* cited by examiner

*Primary Examiner*—Eugene Kim
(74) *Attorney, Agent, or Firm*—Wenderoth, Lind & Ponack, L.L.P.

(57) ABSTRACT

A drug inspection device which makes drug inspection work extremely easy and simple. It has a conveyor for feeding drugs packaged in bags according to prescription data, a camera for taking pictures of drugs in the bags being fed by the conveyor, a camera monitor for displaying one after another the pictures taken by the camera, and a graphic monitor for calling image data to be prescribed from a data base and displaying the thus called data. The picture of the drugs in each bag and the image data on drugs corresponding to the drugs in said each bag are displayed simultaneously on the respective monitors for a predetermined time. By visually checking the monitors, a pharmacist can easily inspect drugs.

7 Claims, 10 Drawing Sheets

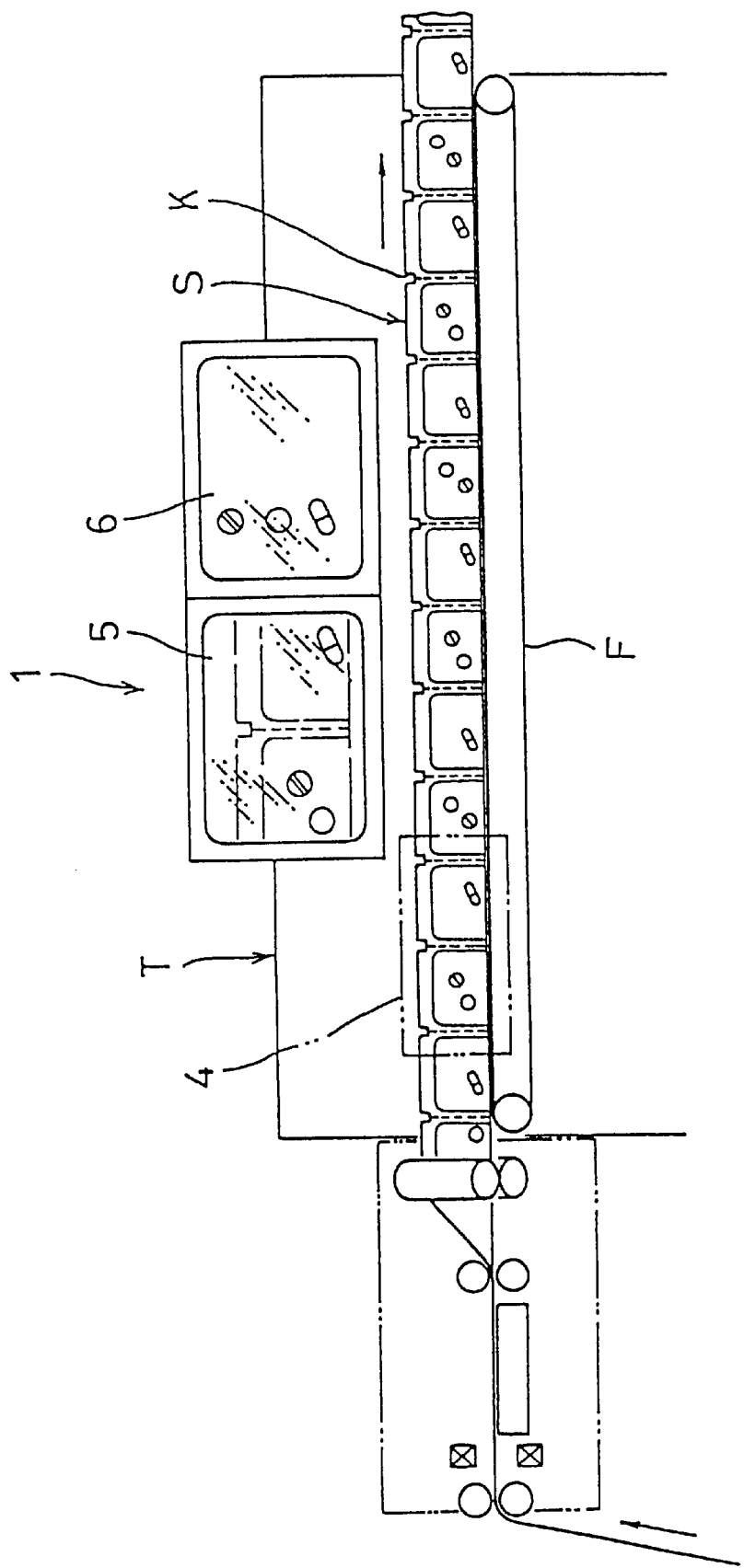

DRUG INSPECTION DEVICE AND DRUG PACKAGING DEVICE

This is a divisional application of Ser. No. 09/301,335, filed Apr. 29, 1999 which is a Continuation-In-Part application of Ser. No. 08/978,605, filed Nov. 26, 1997, now abandoned.

BACKGROUND OF THE INVENTION

This invention relates to a drug inspection device through which pharmacists can inspect packaged medications as prescribed, and a drug packaging device.

Medications prescribed by doctors are packaged by a drug packaging machine and, for the sake of patients' safety, visually checked by pharmacists whether the medications packaged are exactly as prescribed.

Devices are often used which assist pharmacists in inspecting packaged prescriptions, as disclosed in e.g. unexamined Japanese patent publication 7-282219. The device disclosed in this publication has a camera for photographing medications in each bag. A computer processes the picture taken, counts the number of drugs in each bag and determines if the number counted coincides with the prescribed number.

But this device cannot determine the kinds of drugs in each bag. It can only count their number. Thus, pharmacists have to check if the kinds of drugs are correct by directly looking into each bag. If there are a large quantity of drugs to check, pharmacists may sometimes fail to check all the drugs completely.

For speedy and efficient visual checking of drugs, it is essential for pharmacists to memorize the shapes of all the available drugs and their identification codes impressed on individual pieces of drugs. This adds to the burden on pharmacists.

This invention also relates to a drug packaging device including a winder for winding a web of serially connected drug bags around reels for post-treatment.

In hospitals and pharmacies, when drugs prepared according to prescriptions issued by doctors and packaged in bags are handed to patients, pharmacists visually inspect the drugs to check if they are prepared per prescriptions for patients' safety. For such inspection, a drug inspection device such as disclosed in unexamined Japanese patent publication 7-282219 is used as a drug inspection assisting device.

The drug inspection device disclosed in this publication is used exclusively for a specific drug packaging device. Drug bags in which are packaged drugs by a packaging device are automatically and continuously fed through a feed path into the drug inspection device attached to the drug packaging machine, and the drugs are inspected in the drug inspection device by an optical means.

There are a huge variety of drugs. In large hospitals, enormous amounts of drugs are inspected. Pharmacists have to inspect drugs delivered from not one but a plurality of drug packaging devices of different kinds.

Thus, it is an ordinary practice to use a plurality of drug inspection device each for one of the plurality of drug packaging devices. A web of drug bags in which are packaged drugs by a drug packaging device is cut to strips of suitable lengths each for one patient for several days, and the thus cut strips are hand-carried to a drug inspection device for inspection.

Even if strips are hand-carried, when a pharmacist tries to inspect the kind and shape of drugs in the bags with an optical means, it is troublesome to set the bags in the inspection device every time. It is difficult to continuously and efficiently inspect drugs with this method.

An object of this invention is to provide a drug inspection device that takes away most of the burden on pharmacists when they visually check drugs.

Another object of this invention is to provide a drug packaging device having means for winding a web of drug bags by a predetermined length for the convenience of post-processing after packaging such as drug inspection.

SUMMARY OF THE INVENTION

According to this invention, there is provided a drug inspection device comprising a feed means for feeding drugs packaged in bags according to prescription data, a camera means for taking a picture of drugs in each bag which is being fed by the feed means, a first display means for displaying one after another the pictures taken by the camera means, and a second display means for calling image data on the drugs to be prescribed from an image data base and displaying the image data thus called, wherein the picture of drugs in each bag and the image data on drugs corresponding to the drugs in the each bag are displayed simultaneously on the first and second display means for a predetermined of time period.

Picture taken by the camera and the image data for the drugs prescribed are displayed on the display means Drugs can be inspected easily by comparing the camera images and the image data.

The pictures taken by the camera and the graphic images may be selectively displayed on a single monitor by operating a changeover switch. In this arrangement, a pharmacist ordinarily displays only the pictures taken by the camera on the monitor. But if he sees drugs unfamiliar to him on the monitor, he can always change over the monitor screen to the graphic image by operating the changeover switch. After memorizing the shapes and ID codes of the drugs displayed on the monitor, he can change over the switch again to display the camera image back on the monitor and check if the drugs on the monitor are the right ones.

According to this invention, there is also provided a drug packaging device comprising a sheet feed unit for feeding a web of sheet and a packaging unit for separately packaging drugs supplied from a drug supply unit to form drug bags, said drug packaging device comprising a winder for winding a web of drug bags fed from this packaging device.

When drug bags are formed in the drug packaging device and fed out, they are wound by a predetermined length around reels detachably set in the winder. The bags wound around the reels are removed from the winder together with the reels and carried to a post-processing device such as a drug inspection device.

other features and objects of the present invention will become apparent from the following description made with reference to the accompanying drawings, in which:

BRIEF DESCRIPTION OF THE DRAWINGS

FIG. 4 is a view showing the operation of this drug inspection device;

DETAILED DESCRIPTION OF THE PREFERRED EMBODIMENT

An embodiment of the drug packaging device and the drug inspection device as an example of a device for processing drug bags packaged by the drug packaging device according to this invention is described with reference to the attached drawings.

Figure 1:
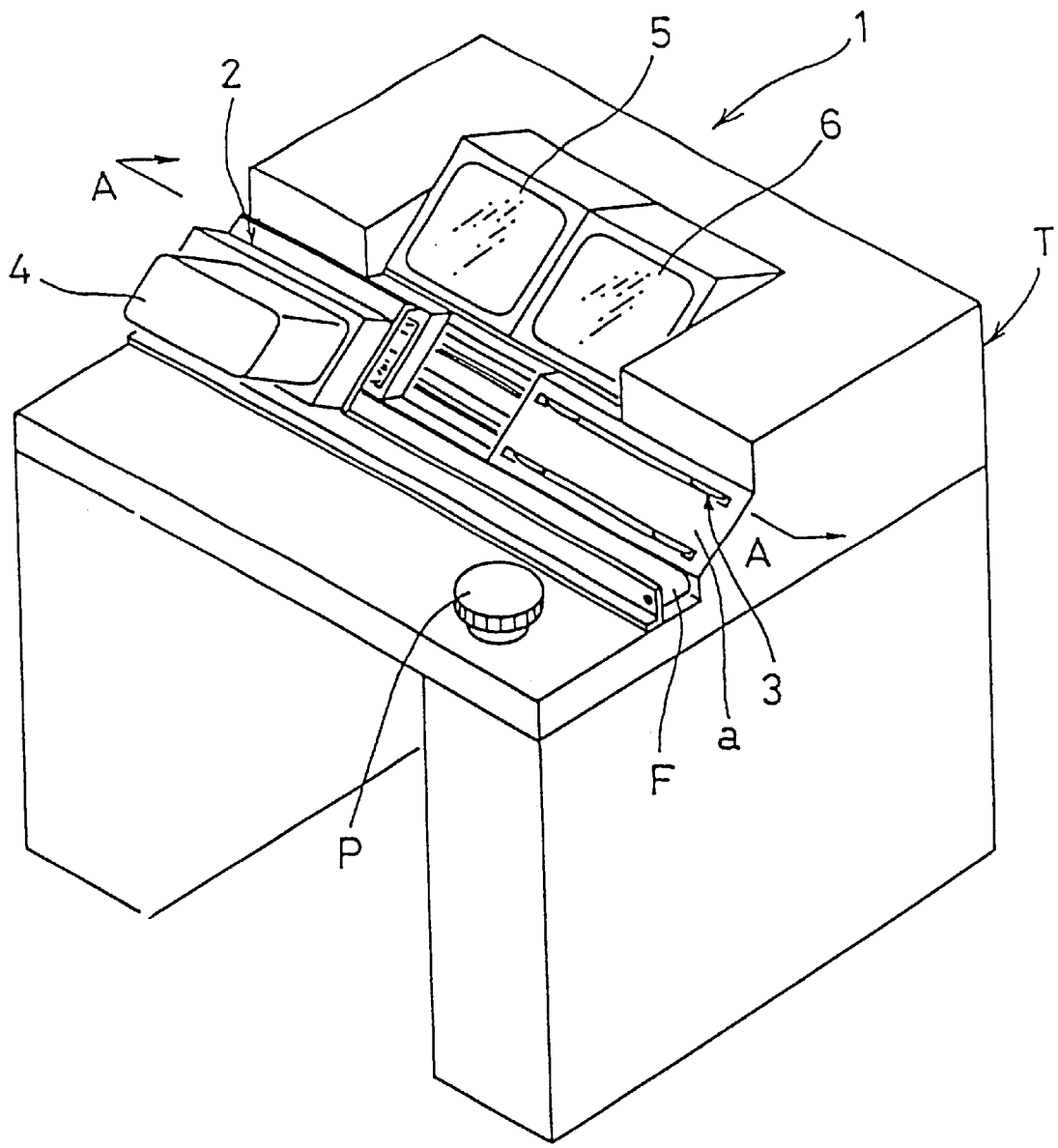
FIG. 1 is a perspective view of an embodiment of the drug inspection device according to this invention.

The drug inspection device 1 shown in FIG. 1 includes a control table T on which are mounted belt conveyors 2, 3 for feeding a strip of series-connected bags from right to left in the figure, a camera 4 for taking pictures of drugs in the respective bags, a camera monitor 5 for displaying the pictures taken by the camera 4, and a graphic monitor 6 for displaying image data of the drugs to be prescribed.

Figure 2:
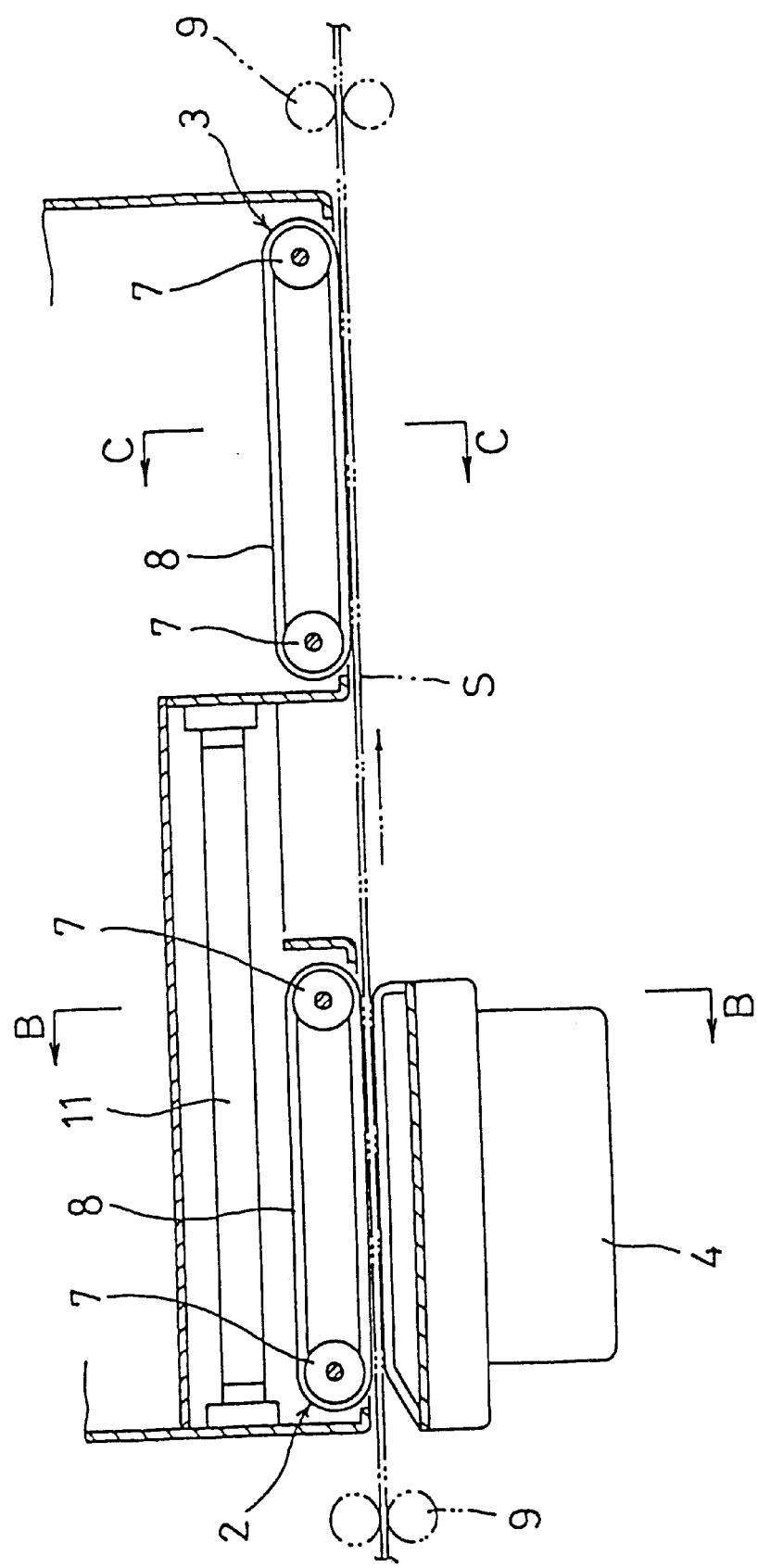
FIG. 2 is a sectional view of the drug inspection device of FIG. 1 taken along line A—A of FIG. 1.

Referring to FIGS. 2 and 3, the right and left belt conveyors 2, 3 are spaced from each other and each comprise a pair of pulleys 7 and a rubber belt 8 running around the pulleys 7. In cooperation with feed rollers 9, the conveyors 2, 3 feed bags S at a constant speed.

Figure 3A:
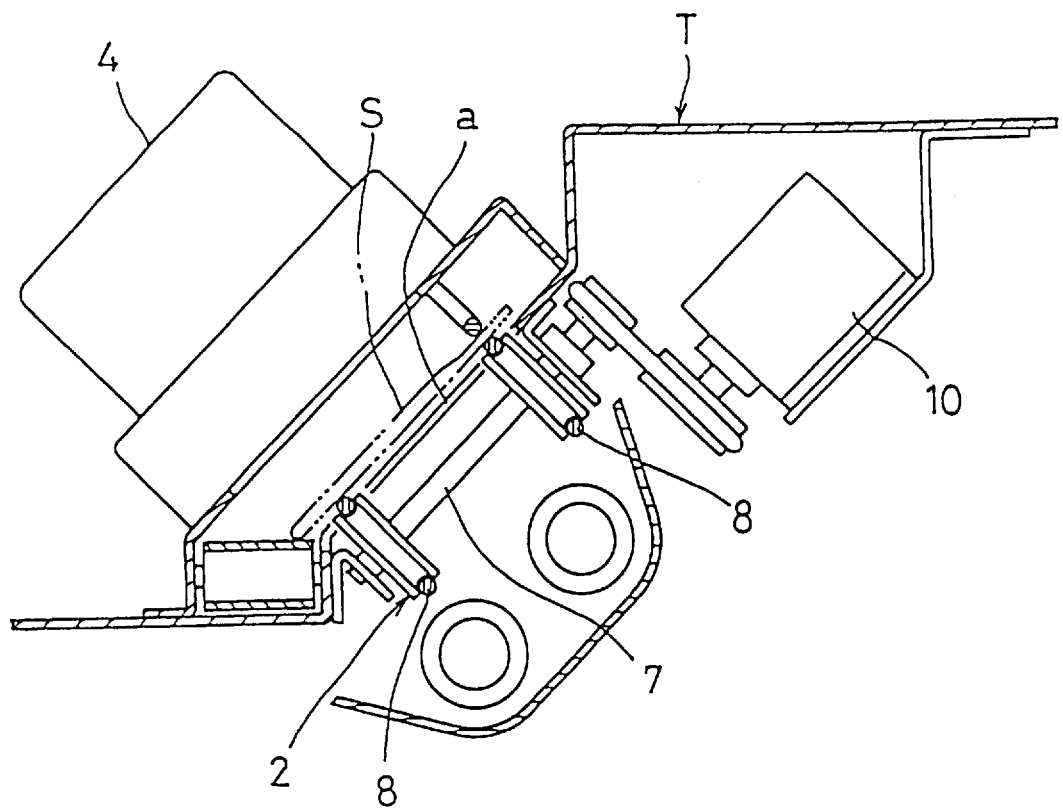
FIG. 3A is a sectional view of the drug inspection device of FIG. 2.
Figure 3B:
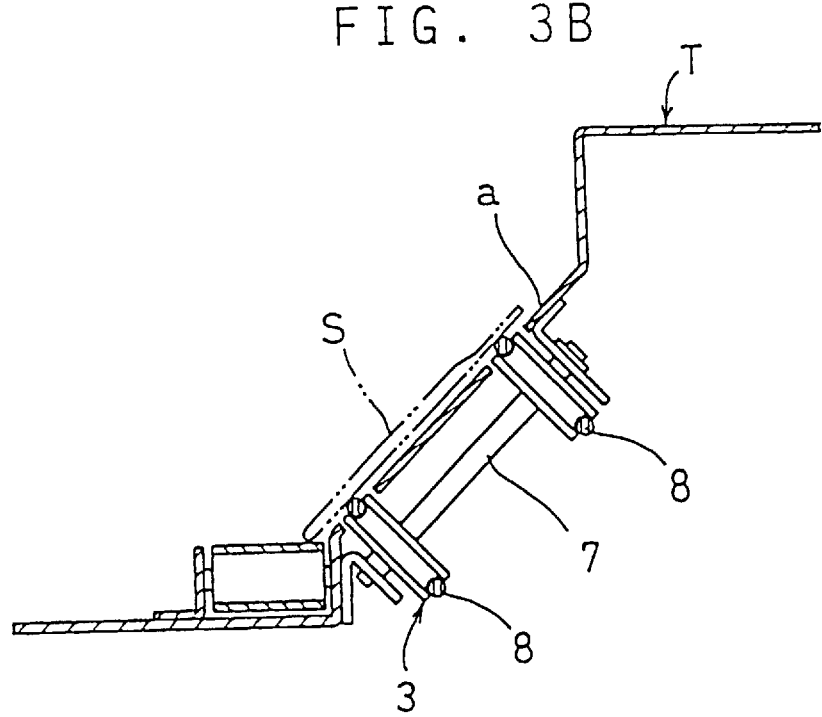
FIG. 3B is a sectional view of the drug inspection device taken along line C—C of FIG. 2.

The rubber belt 8 of each belt conveyor 2, 3 partially protrudes from an inclined feed surface a formed on the control table T (FIG. 3A). The protruding portion of each belt 8 is brought into frictional contact with the bags S on the feed surface a. The bags S are thus fed on the feed surface a by driving the rubber belts 8 with a motor 10 through the respective driving pulleys 7. The other pulleys 7, shown in FIG. 3B, are idler pulleys. Referring to FIG. 1, a flat belt conveyor F is provided on the control table T to support the bottom edges of the bags S being fed by the conveyors 2, 3.

As seen in FIGS. 2 and 3A, the camera 4 is positioned such that it can take a picture of a bag S being fed on the left belt conveyor 2 against backlight from a lamp 11 provided behind the left belt conveyor 2.

Advantageously, drugs in each bag S may be separated from each other by vibrating the bag with a vibrator before taking its picture so that the camera monitor 5 can show all the drugs in the bag clearly with no drugs hidden by others.

The camera 4 takes one after another pictures of the bags S being fed by the belt conveyors 2, 3 and flat belt conveyor F. As shown in FIG. 4, the pictures taken by the camera 4 are displayed one after another on the camera monitor 5 on an enlarged scale, so that pharmacists can clearly see the shapes of drugs and the ID codes impressed thereon.

As shown in FIGS. 1 and 4, the graphic monitor 6 is provided alongside the camera monitor 5. Image data from an image control unit (not shown) in the control table T are displayed on the graphic monitor 6 in the form of computer graphics. Prescription data which are also used by the drug packaging machine are stored in the image control unit. By referring to the prescription data, the image control unit specifies the names of drugs to be put in each bag. Then, the image control unit accesses an image data base (not shown) in the control table T to call image data corresponding to the drugs specified, and transmits the data called to the graphic monitor 6 as image signals.

The image data are digitized data for showing drug shapes (such as tablets and capsules) in the form of computer graphics. If ID codes are impressed on actual drugs, the shape of code-impressed drugs is stored in the image data base as image data.

As described above, the camera monitor 5 displays one after another pictures of the drugs being actually fed by the belt conveyors 2, 3, while the graphic monitor 6 displays one after another graphic images of drugs that should be put in bags S. All what a pharmacist does is then merely to compare the pictures on both monitors and check if they are identical, i.e. if the right drugs are in each bag. The time during which each picture or image is shown on each monitor is adjustable depending on how quickly a pharmacist can compare pictures on both monitors. This time can be changed from one type of drugs to another. Since drugs are shown on an enlarged scale, visual checking of drugs is easy. Pharmacists do not have to memorize all the available drug shapes and their ID numbers. Pharmacists' labor thus lessens to a great degree. If a pharmacist finds anything wrong, he presses an emergency button P on the control table T to stop the belt conveyors 2, 3, and takes any necessary measure.

The drug inspection device 1 has a counter (not shown) for counting the number of notches K (FIG. 4) formed at the boundaries between the adjacent bags S. The counter reports the number counted to a processing unit (not shown) in the control table T. The same prescription data as stored in the image control unit is also stored in the processing unit. By referring to the prescription data, the processing unit determines the number of bags needed and compares this number with the number of notches K counted by the counter to check if the required number of bags are actually formed. If not, a pharmacist is notified of this fact by some kind of alarm.

Figure 5:
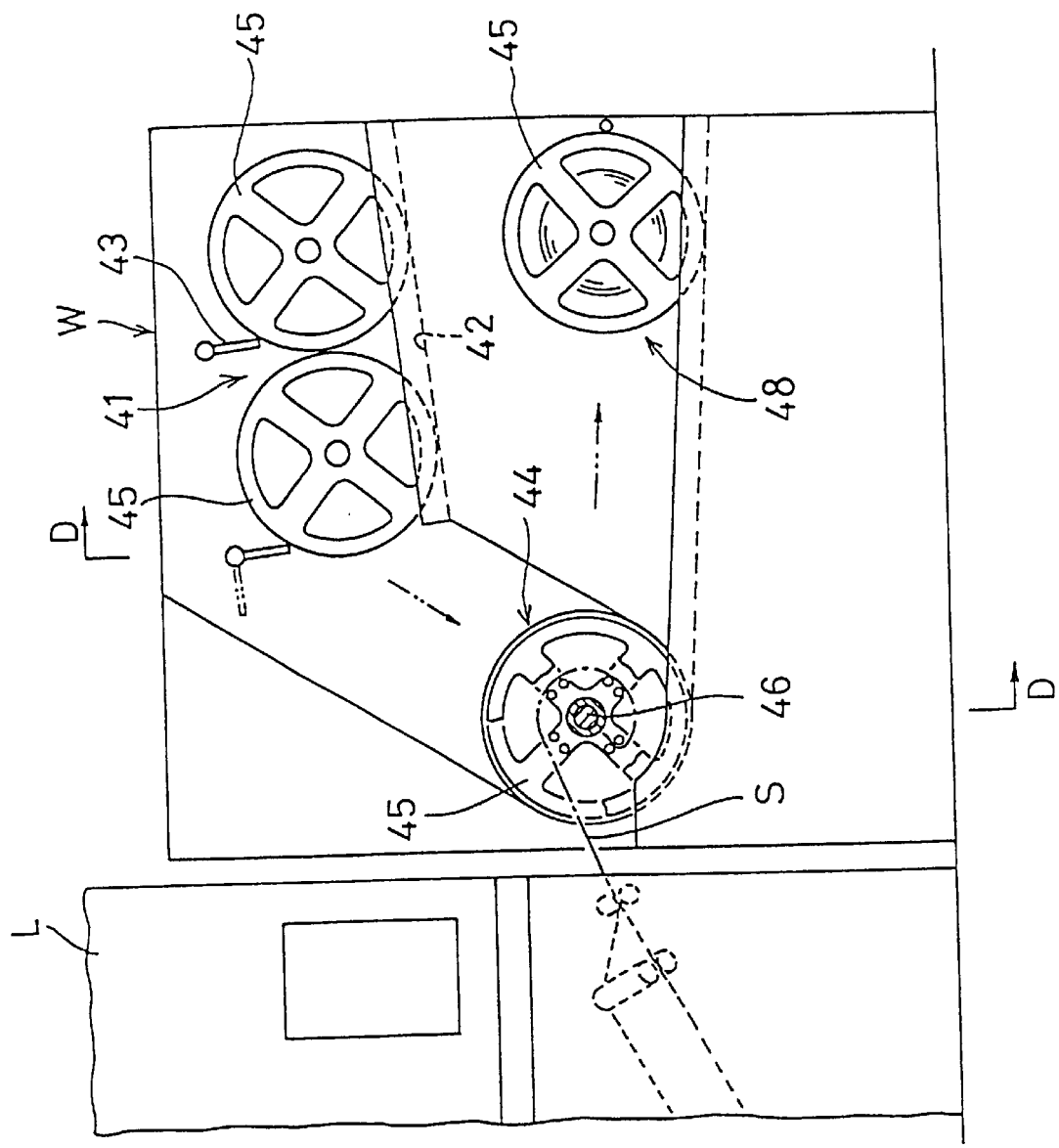
FIG. 5 is a front view of a bag winder.
Figure 6:
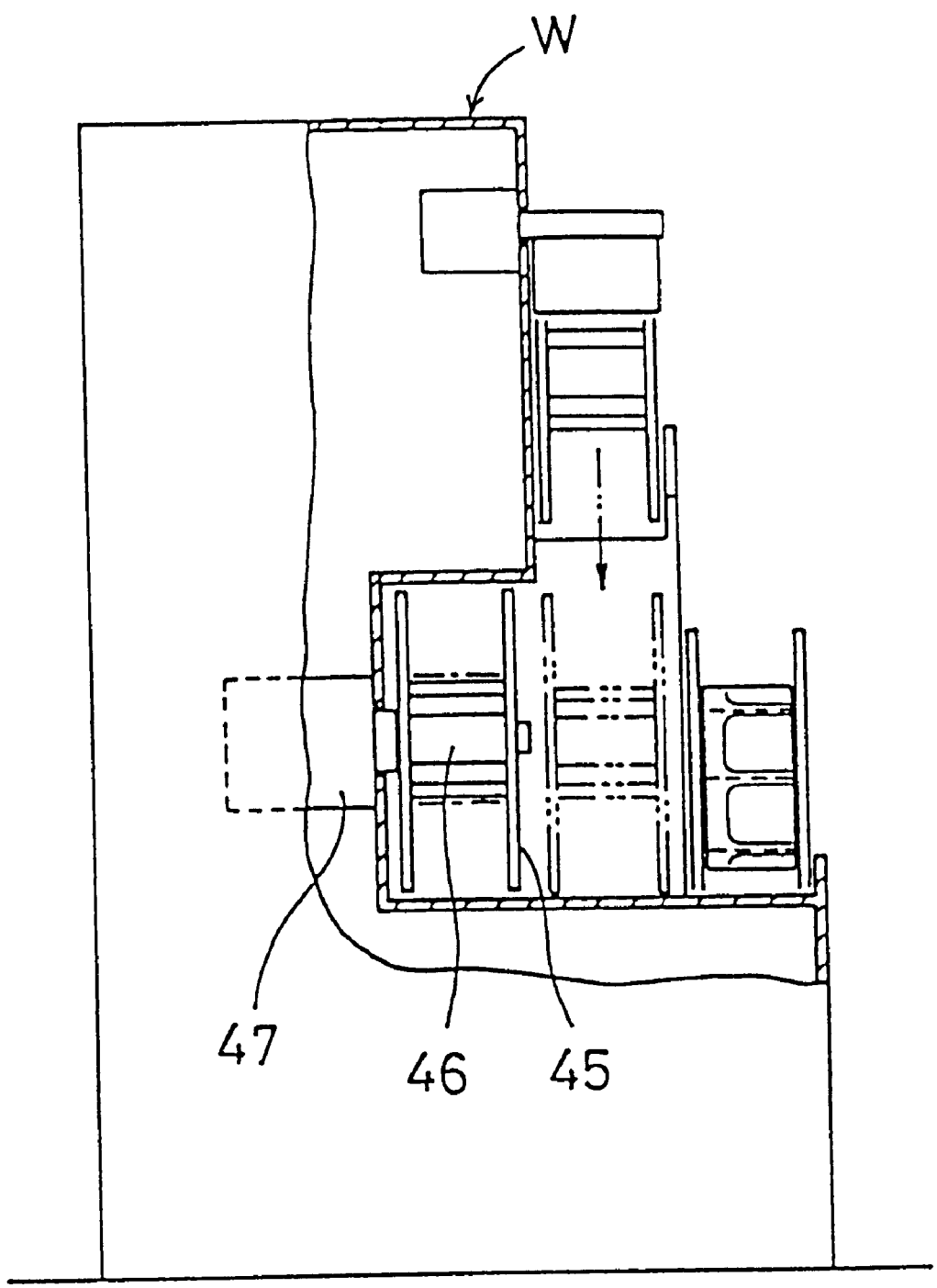
FIG. 6 is a sectional view of the winder taken along line D—D of FIG. 5.

For continuous and efficient processing, serially connected drug bags S to be inspected by the drug inspection device is wound around reels by a predetermined length and fed from the reels. A winder W for this purpose is shown in FIGS. 5 and 6. This winder W is mounted on the drug packaging device L to wind a web of drug bags S fed from the device L around reels 45.

Figure 7:
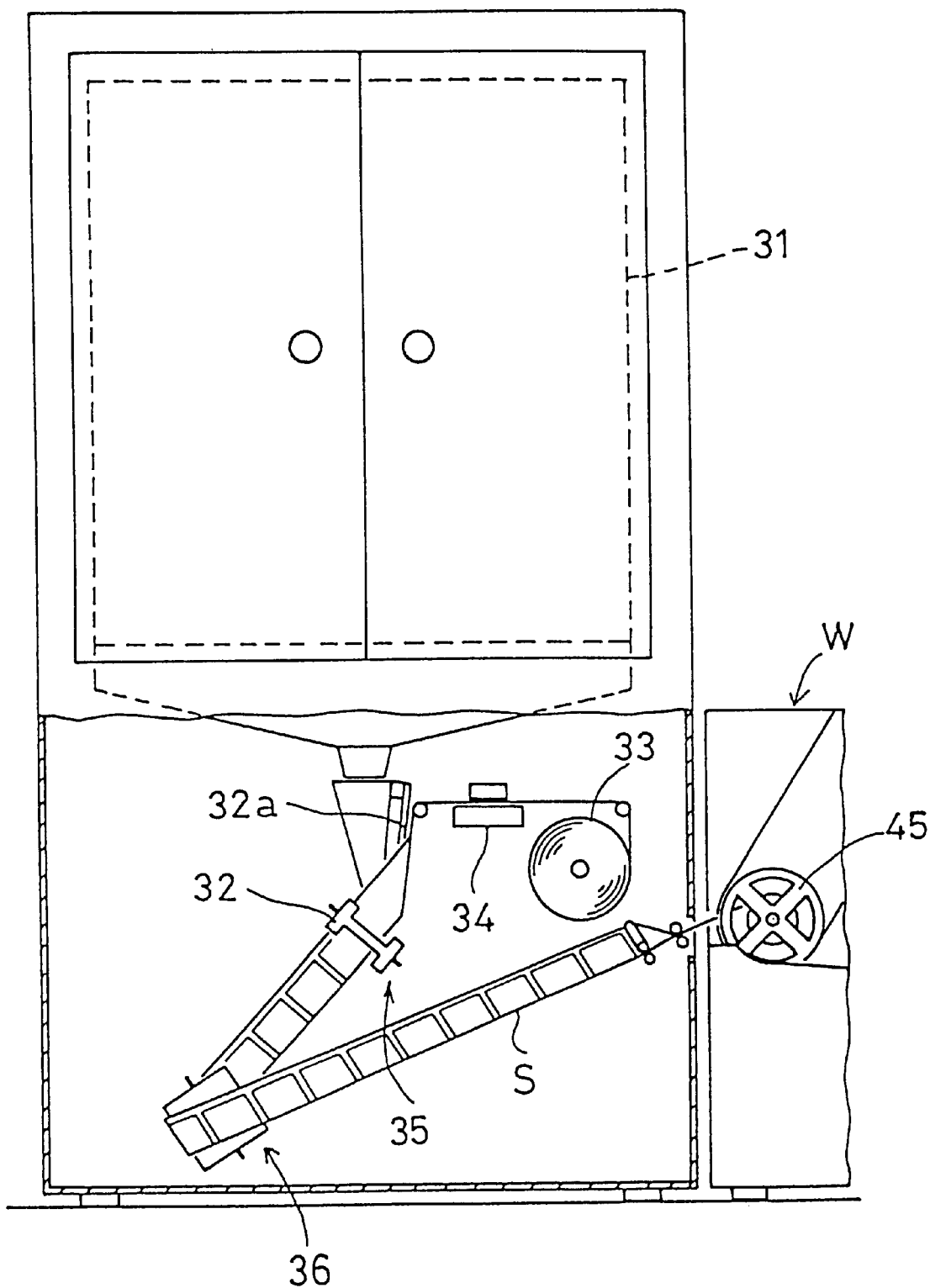
FIG. 7 is a schematic view of a drug packaging device.

For example, the drug packaging device L has, as shown in FIG. 7, a packaging unit 32 under a drug supply unit 31 for storing and supplying drugs such as powder drugs and tablets. It is of a known type such as of the type comprising a feed means for feeding a packaging sheet from a sheet roll in a sheet feed unit 33, a printer 34 for printing drug names and patient names on the sheet, a triangular plate 32a in the packaging unit 32 for folding the sheet in half to receive drugs in the thus folded sheet, and heater rolls 35 for heat-sealing the sheet along both side edges and one end thereof at predetermined intervals to package drugs separately, and means for discharging the bags through a feed path 36. Thus, the drug packaging device L is not limited to the illustrated type but may of any other type.

Referring now to FIGS. 5 and 6, a strip of series-connected bags S formed on a drug packaging machine L are wound on a reel R of a winder W. The winder W stocks a plurality of empty reels 45 on an inclined shelf plate 42 of a stock space 41. To take up drug bags S, one of the reels is set in a take-up station 44. In the take-up station 44, a take-up shaft G is provided which is coupled to and driven by a motor M mounted in the take-up station 44. With an empty reel R mounted on the shaft 46, the tip of the strip of bags S fed from the drug packaging machine L is manually hooked to the reel 47. The motor 47 is activated in this state to wind the strip of bags at the same speed at which the drug packaging machine L discharges the strip of bags S. When the strip is wound by a predetermined length, it is cut. The reel R, on which is now wound the strip of bags S, is dismounted from the shaft G and stocked in the stock space 48.

Figure 8:
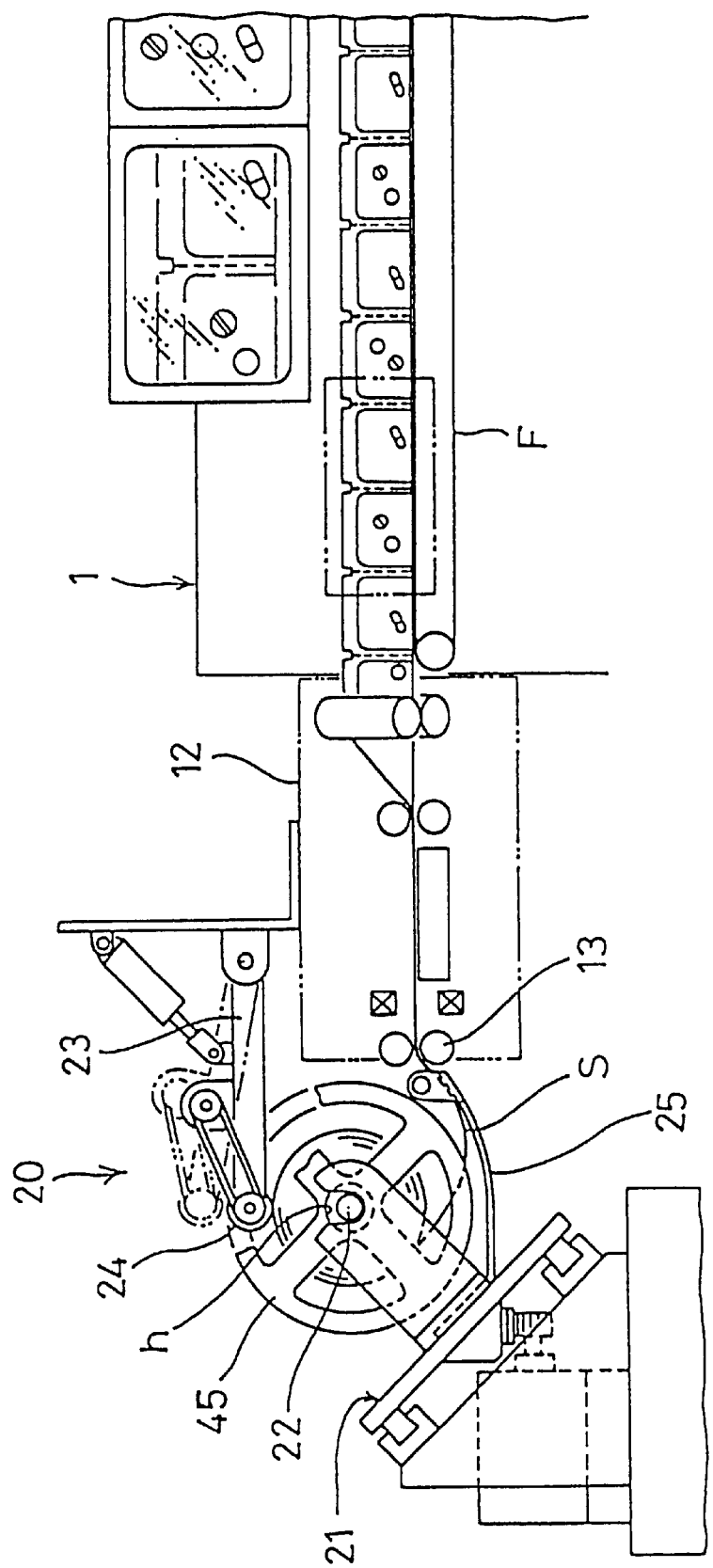
FIG. 8 is a side view of a bag feeder for feeding bags to the drug inspection device.
Figure 9:
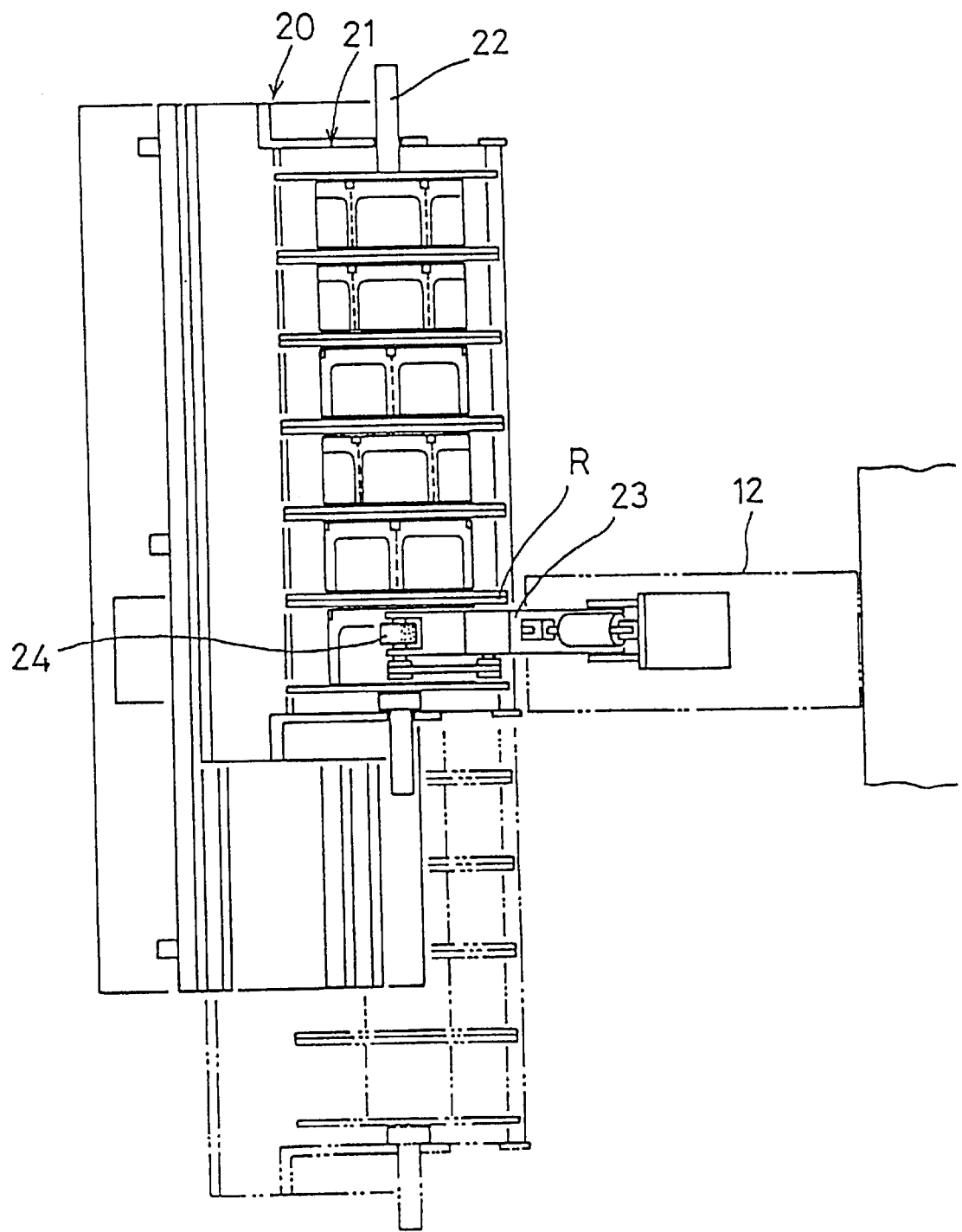
FIG. 9 is a top plan view of the feeder of FIG. 8.

A plurality of such reels 45 are then mounted manually or automatically on a feeder 20 shown in FIGS. 8 and 9. The feeder 20 comprises a rotary shaft 22 mounted on a mounting plate 21 and a driving arm 23 having its tip disposed near the rotary shaft 22. The reels 45 are mounted side by side on the shaft 22 by passing the shaft 22 through holes h of the reels 45. In this state, the reels 45 are freely rotatable about the shaft 22.

With the reels 45 set on the feeder 20, a roller 24 at the tip of the driving arm 23 is in contact with the strip of bags wound on the foremost one of the reels 45 (FIG. 9). Thus, by rotating the roller 24, the foremost reel 45 is rotated about the shaft 22. The mounting plate 21 has a support plate 25 (FIG. 8) curved along the bottom of a reel 45 and having its tip disposed near pinch rollers 13 of a feed unit 12 of the drug inspection device 1.

When the reel 45 is turned by the driving arm 23, the tip of the strip of bags S wound on this reel 45 is pushed out along the top surface of the support plate 25 and caught between the pinch rollers 13. The bags S are thus fed to the belt conveyor 2. When the reel 45 becomes empty, the driving arm 23 is raised, the next reel is moved to the position under the driving arm by advancing the mounting plate 21 as shown in FIG. 9, and the driving arm 23 is lowered.

Figure 10A:
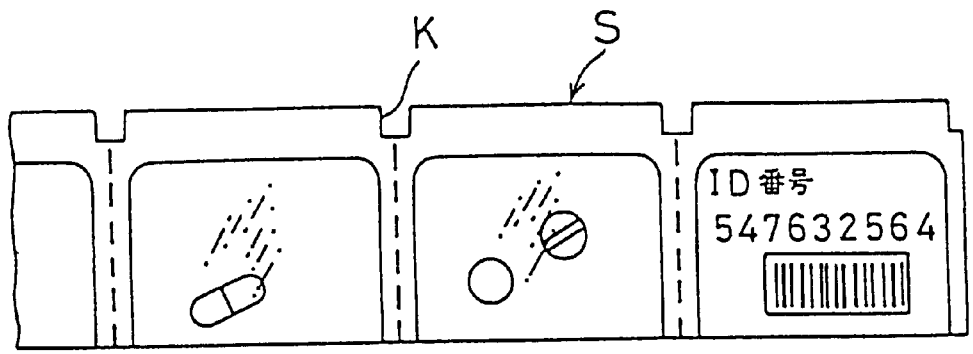
FIGS. 10A–10C are front views of drug packing bags.

In this embodiment, drug names are specified based on the prescription data. But instead, as shown in FIG. 10A, drug names may be specified based on ID numbers printed on bags S. Such ID numbers may be indicated in the form of bar codes so that they can be read by an inexpensive bar code reader.

Figure 10B:
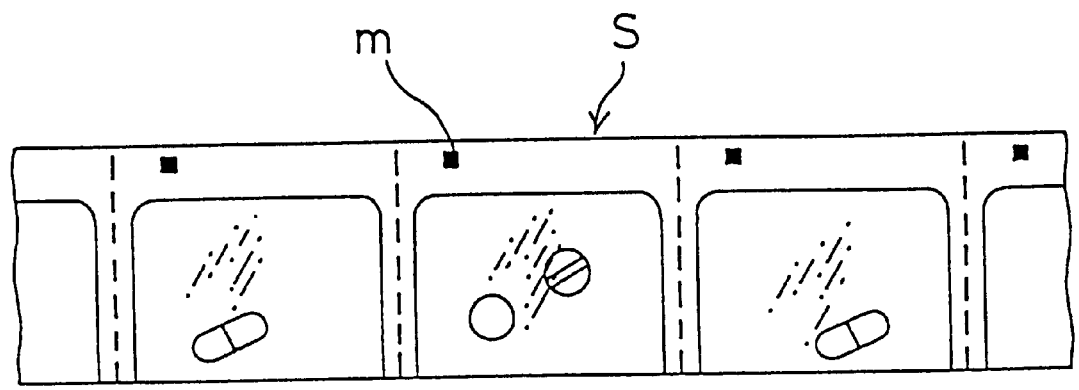
Figure 10C:
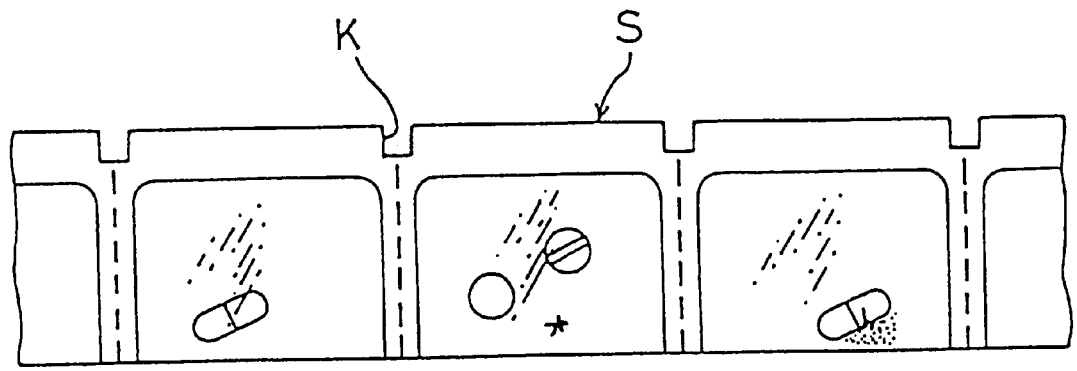

As shown in FIG. 10B, the number of bags may be determined by counting the number of marks m printed on each bag. Drug inspection includes, besides checking if drugs as prescribed are in each bag, checking if any drug is damaged or if any foreign matter is mixed in bags as shown in FIG. 10C.

A computer may be used for automatic drug inspection. Such a computer processes pictures taken by the camera 4, compares the thus processed pictures with the image data from the image data base, and determines whether or not drugs are packaged as prescribed, drugs are damage-free, or bags are free of foreign matter. In this case, a pharmacist checks the monitors 5, 6 as a mere computer backup. The device of the embodiment has two monitors 5, 6. But the pictures taken by the camera and the graphic images may be superimposed on a single monitor.

Otherwise, the pictures taken by the camera and the graphic images may be selectively displayed on a single monitor by means of a changeover switch. In this arrangement, a pharmacist ordinarily displays only the pictures taken by the camera on the monitor. But if he sees drugs unfamiliar to him on the monitor, he can always change over the monitor screen to the graphic image by operating the changeover switch. After memorizing the shapes and ID codes of the drugs displayed on the monitor, he may change over the switch again to display the camera image back on the monitor and checks if the drugs on the monitor are the right ones.

The drug inspection device according to the invention makes drug inspection work by pharmacists extremely easy and simple. Thus, pharmacists can check drugs reliably even if they have a large quantity of drugs to check.

According to this invention, for the convenience of post-processing such as drug inspection, a winder is provided. A web of serially connected drug bags formed by the drug packaging device is wound around reels detachably set on the winder by a predetermined length. Thus, automatic processing is possible simply by hand-carrying and setting the web wound around the reels. This greatly rationalizes post-processing.

What is claimed is:

1. A drug packaging and delivery system comprising:
   a sheet feeder unit for feeding a packaging sheet;
   a packaging unit for forming bags in the packaging sheet, for feeding drugs into each of the bags, and for sealing the bags having the drugs therein so as to form a drug package sheet;
   a winder unit including a plurality of empty reels, said winder unit being adapted to wind a section of the drug package sheet onto each one of the empty reels so as to form a plurality of loaded reels; and
   a drug package feeder unit for unwinding the section of drug package sheet from each of the loaded reels and feeding the section of drug package sheet to a drug inspection device.

2. The drug packaging and delivery system of claim 1, wherein said winder unit includes:
   a driving unit for rotating each of the empty reels; and
   an empty reel stock compartment including a support plate for supporting the empty reels.

3. The drug packaging and delivery system of claim 2, wherein said winder unit further includes:
   a gate in said empty reel stock compartment, said gate being adapted to raise and lower so as to allow each of the empty reels to be moved from said empty reel stock compartment; and
   a loaded reel stock space for storing the loaded reels therein.

4. The drug packaging and delivery system of claim 1, wherein said drug package feeder unit includes:
   a rotary shaft for supporting the loaded reels so as to allow each of the loaded reels to rotate thereon; and
   a driving arm having a roller for contacting the section of the drug package sheet wound on a respective one of the loaded reels, said roller being adapted to rotate while contacting the drug package sheet wound on the respective one of the loaded reels so as to rotate the respective one of the loaded reels.

5. The drug packaging and delivery system of claim 4, wherein said drug package feeder unit further includes:
   pinch rollers for grabbing a tip of the section of the drug package sheet wound on the respective one of the loaded reels; and
   a curved support plate for guiding the tip of the section of the drug package sheet toward said pinch rollers as said roller rotates the respective one of the loaded reels.

6. The drug packaging and delivery system of claim 5, wherein said winder unit includes:

a driving unit for rotating each of the empty reels; and an empty reel stock compartment including a support plate for supporting the empty reels.

7. The drug packaging and delivery system of claim 6, wherein said winder unit further includes:

a gate in said empty reel stock compartment, said gate being adapted to raise and lower so as to allow each of the empty reels to pass from said empty reel stock compartment; and a loaded reel stock space for storing the loaded reels therein.

\* \* \* \* \*